(12) United States Patent
Kassab et al.

(10) Patent No.: US 11,844,622 B2
(45) Date of Patent: Dec. 19, 2023

(54) DEVICES, SYSTEMS, AND METHODS FOR GENERATING AND DISPLAYING LARGE BOWEL INFORMATION

(71) Applicant: GI Bionics LLC, San Diego, CA (US)

(72) Inventors: Ghassan S. Kassab, La Jolla, CA (US); Hans Gregersen, Ma On Shan (HK)

(73) Assignee: GI Bionics, LLC, San Diego, CA (US)

( * ) Notice: Subject to any disclaimer, the term of this patent is extended or adjusted under 35 U.S.C. 154(b) by 450 days.

(21) Appl. No.: 16/442,233

(22) Filed: Jun. 14, 2019

(65) Prior Publication Data

US 2019/0380640 A1 Dec. 19, 2019

Related U.S. Application Data

(60) Provisional application No. 62/685,185, filed on Jun. 14, 2018.

(51) Int. Cl.
| | | |
|---|---|---|
| *A61B 5/00* | (2006.01) | |
| *A61B 5/107* | (2006.01) | |
| *A61B 5/1455* | (2006.01) | |
| *A61B 5/0538* | (2021.01) | |
| *G16H 50/50* | (2018.01) | |
| *A61B 5/145* | (2006.01) | |

(52) U.S. Cl.
CPC .......... *A61B 5/4255* (2013.01); *A61B 5/0002* (2013.01); *A61B 5/0538* (2013.01); *A61B 5/1076* (2013.01); *A61B 5/1079* (2013.01); *A61B 5/1455* (2013.01); *A61B 5/14539* (2013.01); *G16H 50/50* (2018.01); *A61B 2562/0219* (2013.01); *A61B 2562/0247* (2013.01)

(58) Field of Classification Search
CPC .... A61N 1/36007; A61N 1/0507; A61B 5/42; A61B 5/0002; A61B 5/0538; A61B 5/1076; A61B 5/1079; A61B 5/14539; A61B 5/1455; A61B 2562/0219; A61B 2562/0247; G06T 2207/30004
See application file for complete search history.

(56) References Cited

U.S. PATENT DOCUMENTS

2007/0135803 A1* 6/2007 Belson ............... A61B 1/00154
606/1

FOREIGN PATENT DOCUMENTS

WO WO-2015151098 A2 * 10/2015 ............... A61B 1/00

* cited by examiner

Primary Examiner — Deborah L Malamud

(57) ABSTRACT

Devices, systems, and methods for generating and displaying large bowel information. In at least one embodiment of a method of generating a gastrointestinal model, comprising the steps of obtaining size data within a mammalian gastrointestinal tract using a device configured to fit within the mammalian gastrointestinal tract, and modifying a model colon using the obtained size data to generate a patient-specific colon model.

8 Claims, 15 Drawing Sheets

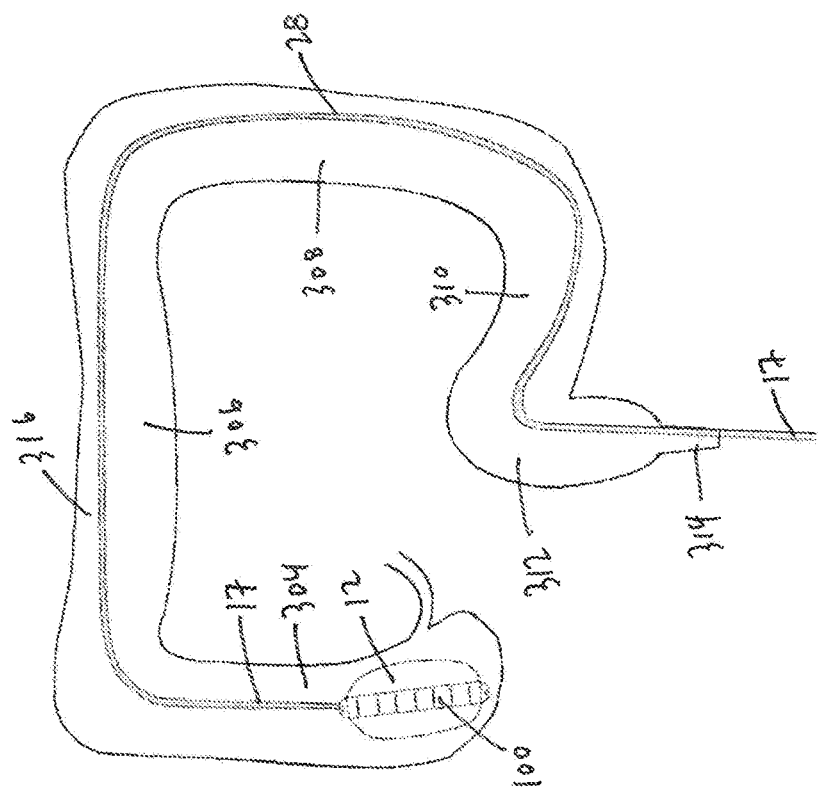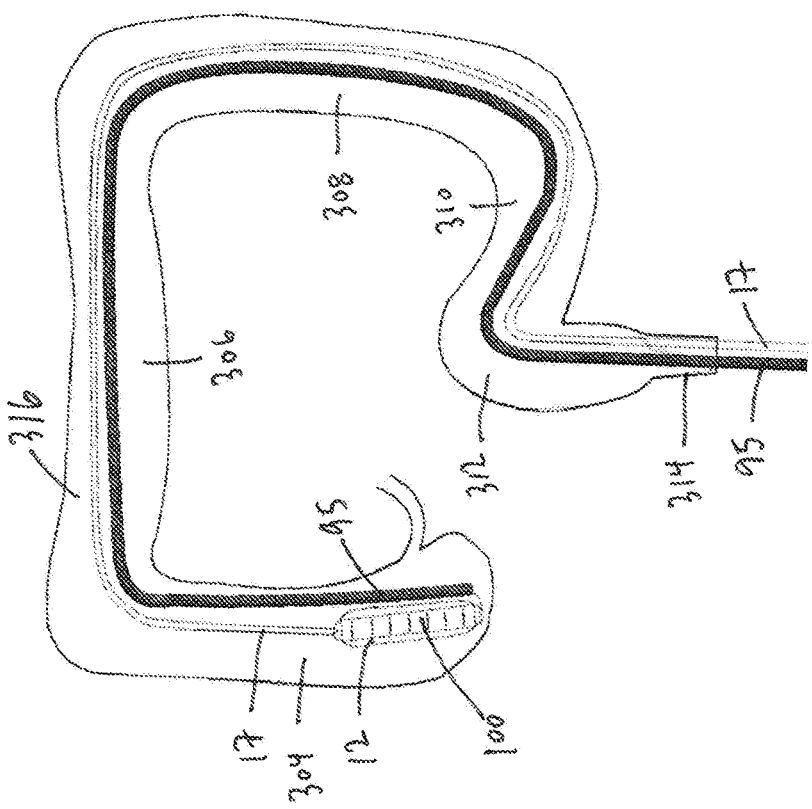

DEVICES, SYSTEMS, AND METHODS FOR GENERATING AND DISPLAYING LARGE BOWEL INFORMATION

PRIORITY

The present patent application is related to, and claims the priority benefit of, U.S. Provisional Patent Application Ser. No. 62/685,185, filed on Jun. 14, 2018, the contents of which are hereby incorporated by reference in their entirety into this disclosure.

BACKGROUND

Obtaining data relative to a large bowel is generally difficult and/or expensive to accomplish, with said data generally obtained using external scans and not in connection with the excretory process. Devices, systems, and methods configured to obtain large bowel data with the large bowel at various locations within the large bowel would be greatly appreciated within the medical arts.

BRIEF SUMMARY

The present disclosure includes disclosure of a visual model for displaying device data over time in connection with a model large bowel. Various devices can be used within the large bowel to obtain data/information, which can be transmitted from said device to an external system, such as a computer, which can then process said data/information and used the same to generate a visual model of the large bowel of the patient using said device.

The present disclosure includes disclosure of methods for obtaining and depicting large bowel data/information, as referenced and/or shown herein.

The present disclosure includes disclosure of systems for use with devices for obtaining and depicting large bowel data/information, as referenced and/or shown herein.

The present disclosure includes disclosure of using devices to obtain large bowel data/information that can be depicted, as referenced and/or shown herein.

The present disclosure includes disclosure of a method of generating a gastrointestinal model, comprising the steps of obtaining size data within a mammalian gastrointestinal tract using a device configured to fit within the mammalian gastrointestinal tract, and modifying a model colon using the obtained size data to generate a patient-specific colon model.

The present disclosure includes disclosure of a method of generating a gastrointestinal model, wherein the step of obtaining size data comprises the steps of obtaining ascending colon size data, obtaining transverse colon size data, obtaining descending colon size data, and obtaining sigmoid colon size data.

The present disclosure includes disclosure of a method of generating a gastrointestinal model, wherein the step of obtaining size data further comprises the steps of obtaining rectum size data.

The present disclosure includes disclosure of a method of generating a gastrointestinal model, wherein the step of obtaining size data further comprises the step of obtaining anal canal size data during defecation of the device.

The present disclosure includes disclosure of a method of generating a gastrointestinal model, wherein the obtained size data comprises at least one diameter obtained within the gastrointestinal tract, and wherein the step of modifying the model colon is performed by modifying the model colon at a corresponding location of the device when the at least one diameter is obtained so that the generated patient-specific colon model includes an indication of the at least one diameter therein.

The present disclosure includes disclosure of a method of generating a gastrointestinal model, wherein the obtained size data comprises at least one cross-sectional area obtained within the gastrointestinal tract, and wherein the step of modifying the model colon is performed by modifying the model colon at a corresponding location of the device when the at the least one cross-sectional area is obtained so that the generated patient-specific colon model includes an indication of the at least one cross-sectional area therein.

The present disclosure includes disclosure of a method of generating a gastrointestinal model, wherein the obtained size data comprises data obtained at a first location and at a second location within the gastrointestinal tract, and wherein the step of modifying the model colon is performed by modifying the model colon to reflect a distance between the first location and the second location so that the generated patient-specific colon model includes an indication of the distance therein.

The present disclosure includes disclosure of a method of generating a gastrointestinal model, wherein the step of modifying the model colon is performed using a console or computer having a processor connected or otherwise in communication with a storage medium, whereby computer instructions stored within the storage medium are accessible by the processor to operate the console or computer to obtain the size data from the device and to process the same to modify the model colon and to display the patient-specific colon model on an output device operably connected to or formed as part of the console or computer.

The present disclosure includes disclosure of a method of generating a gastrointestinal model, wherein the size data is obtained from the device wirelessly.

The present disclosure includes disclosure of a method of generating a gastrointestinal model, further comprising the step of obtaining additional data within the mammalian gastrointestinal tract, the additional data selected from the group consisting of impedance data obtained using an impedance element, pressure data obtained using a pressure sensor, pH data obtained using a pH sensor, and visual data obtained using a camera.

The present disclosure includes disclosure of a method of generating a gastrointestinal model, wherein the step of obtaining size data is performed using the device comprising a central stabilizing core at least partially surrounded by a balloon or bag, a front-positioned pressure sensor, a front-positioned gyroscopic sensor, a rear-positioned pressure sensor, a rear-positioned gyroscopic sensor, and a wireless transmitter The present disclosure includes disclosure of a device configured to perform an exemplary method of the present disclosure, the device comprising a central stabilizing core at least partially surrounded by a balloon or bag, a front-positioned pressure sensor configured to obtain front pressure data within the mammalian gastrointestinal tract at a relative front of the device, a front-positioned gyroscopic sensor configured to obtain front gyroscopic data within the mammalian gastrointestinal tract at a relative front of the device, a rear-positioned pressure sensor configured to obtain rear pressure data within the mammalian gastrointestinal tract at a relative rear of the device, a rear-positioned gyroscopic sensor configured to obtain rear gyroscopic data within the mammalian gastrointestinal tract at a relative rear of the device, and a wireless transmitter configured to transmit the size data, the front pressure data, the front gyroscopic data, the rear pressure data, and the rear gyroscopic data to a computer or console configured to receive the same.

The present disclosure includes disclosure of a device, further comprising an impedance element configured to obtain impedance data within the mammalian gastrointestinal tract.

The present disclosure includes disclosure of a device, further comprising a power source configured to power at least one of the front-positioned pressure sensor, the front-positioned gyroscopic sensor, the rear-positioned pressure sensor, the rear-positioned gyroscopic sensor, the impedance element, and/or the wireless transmitter.

The present disclosure includes disclosure of a device configured to fit within a mammalian gastrointestinal tract and to obtain data therein, the device comprising a central stabilizing core at least partially surrounded by a balloon or bag, a front-positioned pressure sensor configured to obtain front pressure data within the mammalian gastrointestinal tract at a relative front of the device, a front-positioned gyroscopic sensor configured to obtain front gyroscopic data within the mammalian gastrointestinal tract at a relative front of the device, a rear-positioned pressure sensor configured to obtain rear pressure data within the mammalian gastrointestinal tract at a relative rear of the device, a rear-positioned gyroscopic sensor configured to obtain rear gyroscopic data within the mammalian gastrointestinal tract at a relative rear of the device, and a wireless transmitter configured to transmit the size data, the front pressure data, the front gyroscopic data, the rear pressure data, and the rear gyroscopic data to a computer or console configured to receive the same.

The present disclosure includes disclosure of a device, further comprising an impedance element configured to obtain impedance data within the mammalian gastrointestinal tract, and a power source configured to power at least one of the front-positioned pressure sensor, the front-positioned gyroscopic sensor, the rear-positioned pressure sensor, the rear-positioned gyroscopic sensor, the impedance element, and/or the wireless transmitter.

The present disclosure includes disclosure of a device, wherein the wireless transmitter is configured to transmit all data obtained by the device to the computer or console, and wherein the computer or console is configured to display front pressure data, rear pressure data, cross-sectional area data based upon the impedance data, and bending data based upon the front gyroscopic data and the rear gyroscopic data, on an output device operably connected to or formed as part of the console or computer.

The present disclosure includes disclosure of a device, further comprising an electrical stimulating element configured to deliver an electric current to the mammalian gastrointestinal tract to stimulate larger bowel motility.

The present disclosure includes disclosure of a device, configured for operation during defecation.

The present disclosure includes disclosure of a device, configured to reversibly couple to an insertion device configured to facilitate insertion and placement of the device within the mammalian gastrointestinal tract.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 17 shows a device positioned within the ascending colon, delivered using an insertion device and having a tube coupled to the device, according to an exemplary embodiment of the present disclosure; and FIG. 18 shows a device positioned within the ascending colon and having a tube coupled to the device for inflation of a balloon or bag of the device, according to an exemplary embodiment of the present disclosure.

Figure 1:
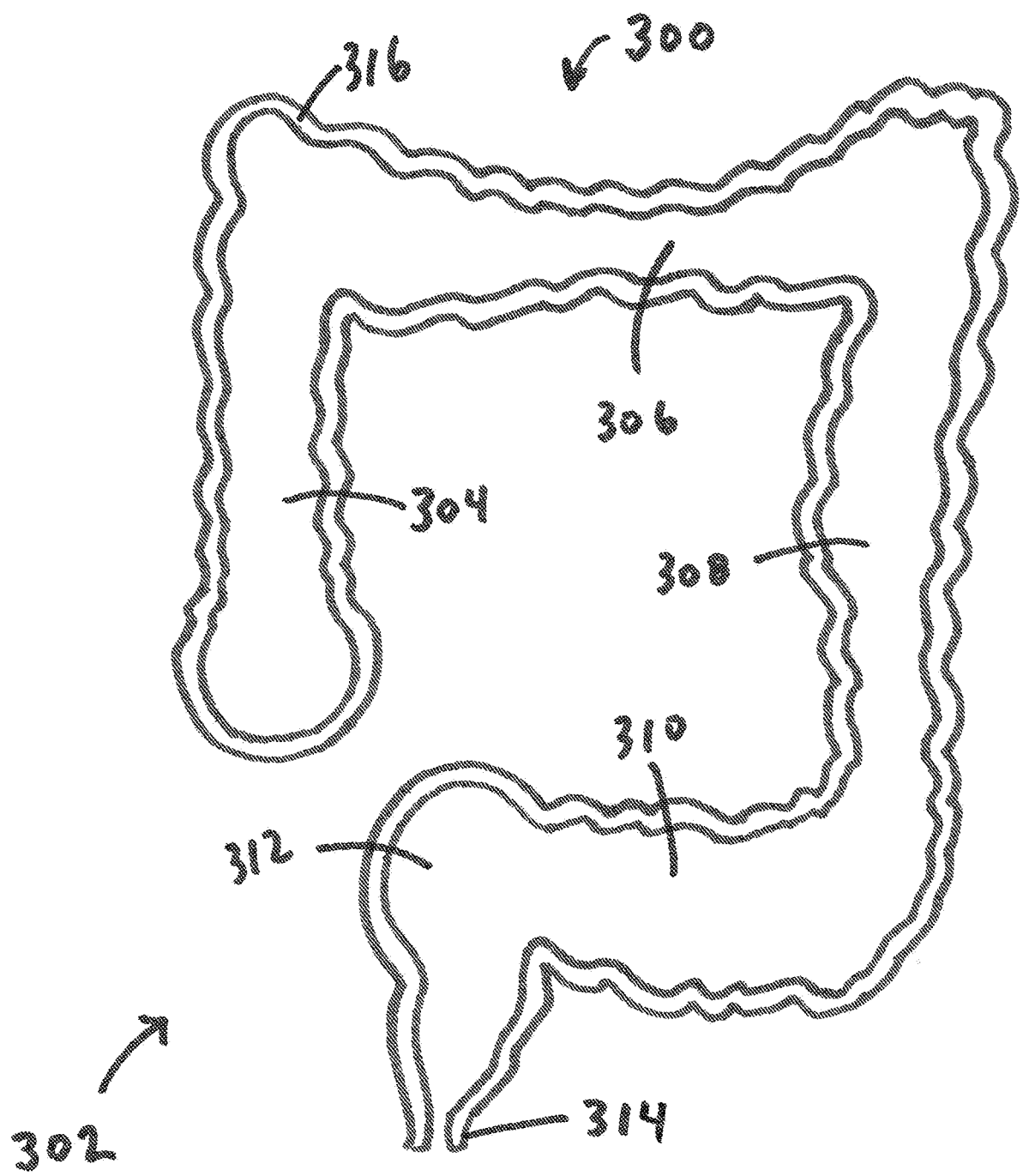
FIG. 1 shows a visual model of a large bowel showing various portions of the large bowel, according to an exemplary embodiment of the present disclosure.

As such, an overview of the features, functions and/or configurations of the components depicted in the various figures will now be presented. It should be appreciated that not all of the features of the components of the figures are necessarily described and some of these non-discussed features (as well as discussed features) are inherent from the figures themselves. Other non-discussed features may be inherent in component geometry and/or configuration. Furthermore, wherever feasible and convenient, like reference numerals are used in the figures and the description to refer to the same or like parts or steps. The figures are in a simplified form and not to precise scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In an exemplary embodiment, and as shown in FIG. 1, visual model 300 is shown (such as which could be depicted or indicated on a display 208, such as two dimensionally or in a three-dimensional way by way of use of a display 208 (such as a projector display) configured to display information in three dimensions), and includes a visual depiction of at least part of a large bowel (a large bowel depiction 302). Large bowel depiction 302, in at least one embodiment, depicts the ascending colon 304, the transverse colon 306, the descending colon 308, the sigmoid colon 310, the rectum 312, and the anal canal 314), or at least one of said depictions/junctions. Large bowel depiction 302 can be based on average human published data, a human model, actual human data, etc.

Figure 2:
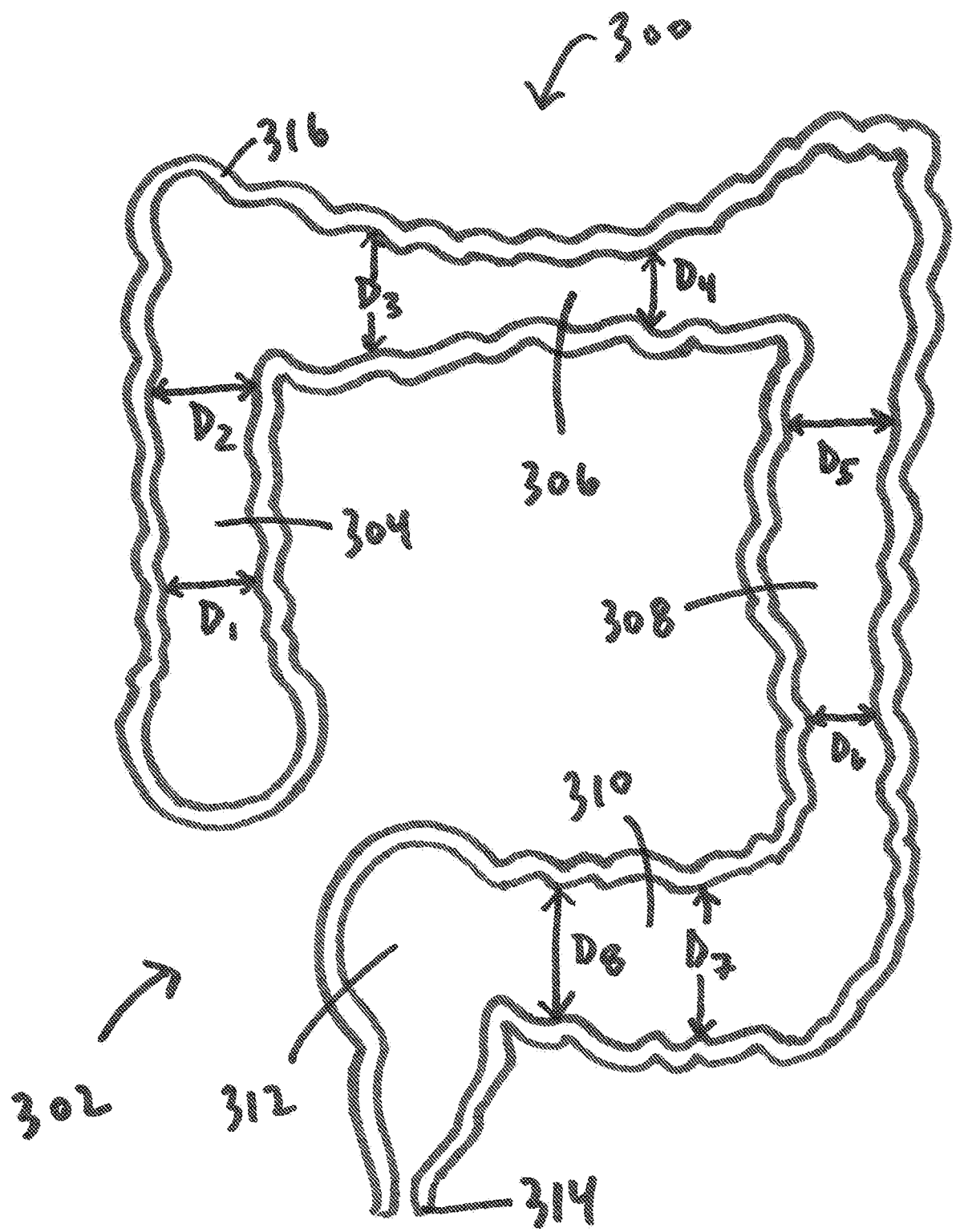
FIG. 2 shows a visual model of a large bowel showing various large bowel diameters, according to an exemplary embodiment of the present disclosure.
Figure 3:
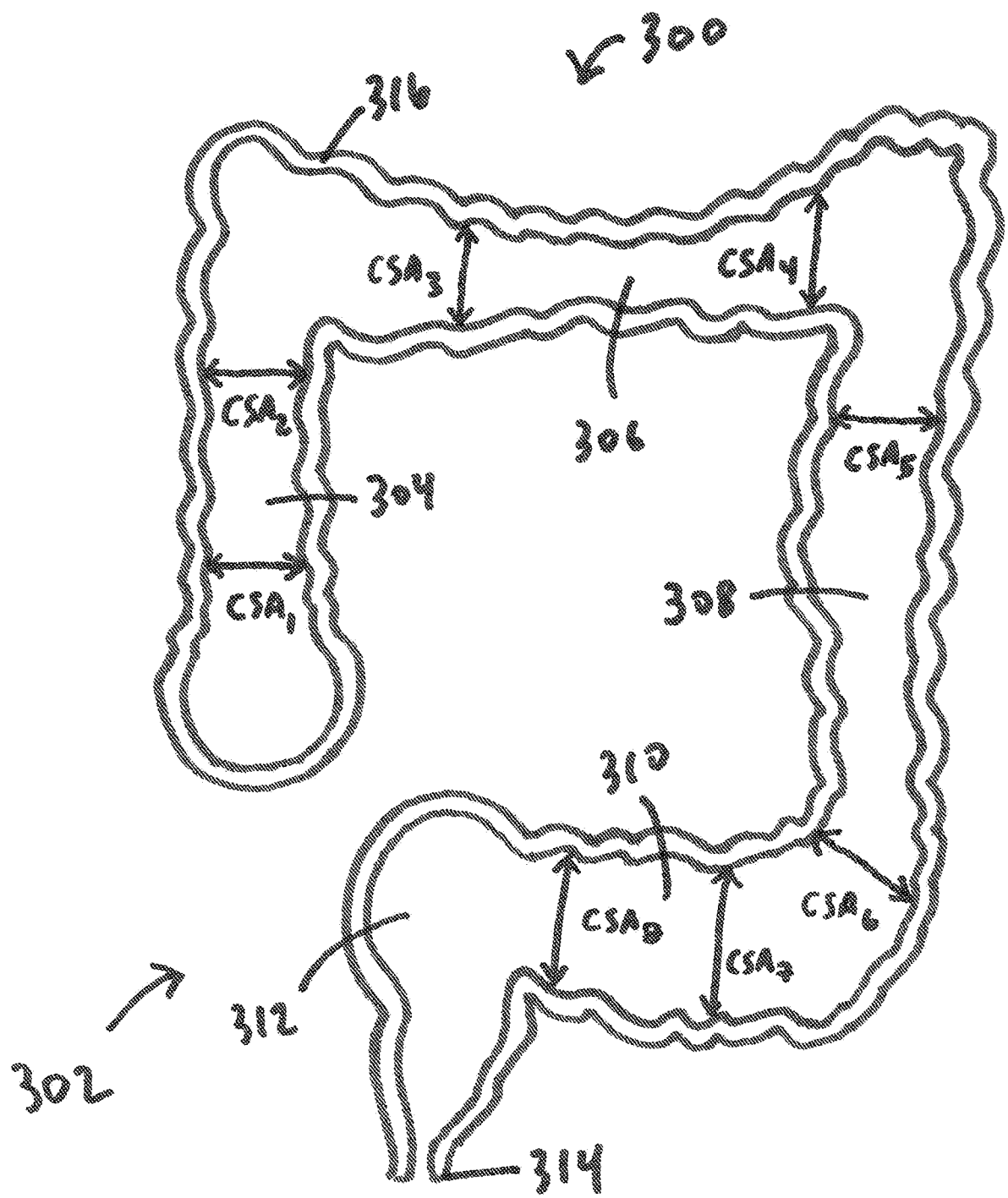
FIG. 3 shows a visual model of a large bowel showing various large bowel cross-sectional areas, according to an exemplary embodiment of the present disclosure.
Figure 4:
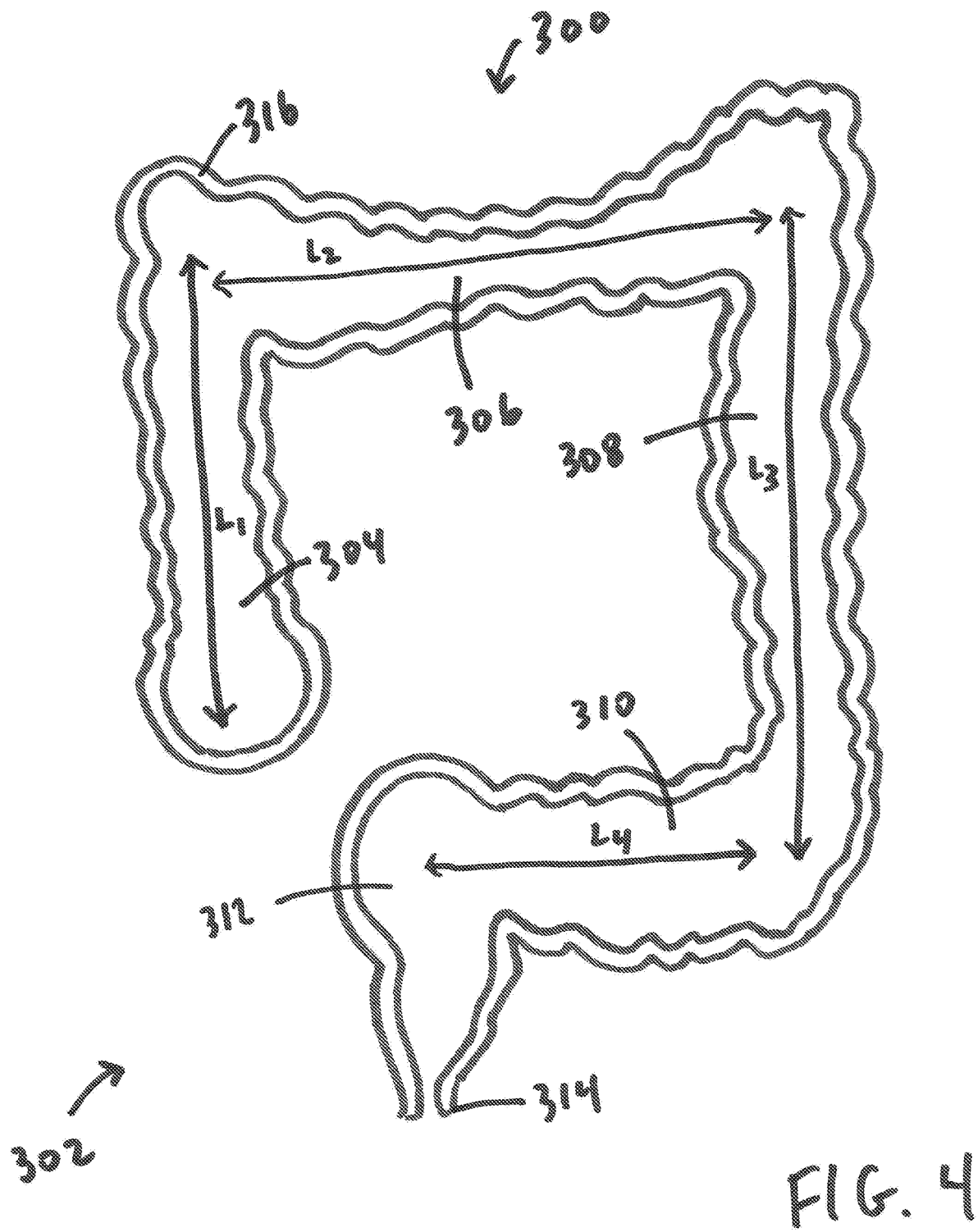
FIG. 4 shows a visual model of a large bowel showing various large bowel portion lengths, according to an exemplary embodiment of the present disclosure.

Large bowel depiction 302 can depict an overall geometry with various large bowel 316 diameters, cross-sectional areas, and/or segment lengths. For example, and as shown in FIG. 2, large bowel depiction 302 can indicate various diameters (Ds), such as $D_1$ and $D_2$ (exemplary diameters of portions of ascending colon 304), such as $D_3$ and $D_4$ (exemplary diameters of portions of transverse colon 306), such as $D_5$ and $D_6$ (exemplary diameters of portions of descending colon 308), and such as $D_7$ and $D_8$ (exemplary diameters of portions of sigmoid colon 310). As shown in FIG. 3, large bowel depiction 302 can indicate (or also indicate in addition to various diameters) various cross-sectional areas (CSAs), such as $CSA_1$ and $CSA_2$ (exemplary diameters of portions of ascending colon 304), such as $CSA_3$ and $CSA_4$ (exemplary diameters of portions of transverse colon 306), such as $CSA_5$ and $CSA_6$ (exemplary diameters of portions of descending colon 308), and such as $CSA_7$ and $CSA_8$ (exemplary diameters of portions of sigmoid colon 310). As shown in FIG. 4, large bowel depiction 302 can indicate (or also indicate in addition to various diameters and/or cross-sectional areas) various segment lengths (Ls), such as $L_1$ (an exemplary length of ascending colon 304), $L_2$ (an exemplary length of transverse colon 306), $L_3$ (an exemplary length of descending colon 308), and $L_4$ (an exemplary length of sigmoid colon 310). Furthermore, various pressure measurements, pH measurements, gyroscopic measurements, camera images, etc., can be obtained using device or capsule 100 of the present disclosure at various locations with the large bowel 316.

As the fecobionic device (an exemplary device or capsule 100, such as disclosed within PCT patent application serial no. PCT/US2017/044707, filed Jul. 31, 2017 and published as PCT patent application publication no. WO 2018/026720 A1 on Feb. 8, 2018, or such as disclosed within U.S. patent application Ser. No. 15/664,938, filed Jul. 31, 2017 and published as U.S. patent application publication no. US 2017/0340264 on Nov. 30, 2017, the contents of each of these two patent applications incorporated herein by reference) transverses the large bowel 316 and obtains information on the diameter, cross-sectional area, or other dimensional/geometric information of the large bowel 316 at one or more locations within the large bowel 316, this information is then used to evolve/generate a patient-specific geometry. In particular, the large bowel 316 can be generally depicted as the large bowel depiction 302 of the visual model 300, and as a device or capsule 100 obtains data within the large bowel 316, various diameters, cross-sectional areas, and/or lengths of large bowel 316 portions can be determined from said data, and the visual model 300, which may start with a generic shape, can be modified or otherwise shown as being specific to the patient using the device or capsule 100.

Movement sensors of the device, such as gyroscopic and accelerometer sensors being an additional element 132 of a device or capsule 100 (as referenced within PCT patent application serial no. PCT/US2017/044707) also yield information on the position/location and the length of the large bowel 316 segments, and as the device or capsule 100 turns from one portion of the large bowel 316 to another (such as from the right to left colon 316) as detected by the gyroscopic angle measurements from one segment to the other, the lengths also updated accordingly. As the device or capsule 100 completes the travel through the large bowel 316 and is expelled or defecated, a complete patient specific anatomy can be displayed demonstrating the proper geometry and dimensions of the large bowel 316 including the ano-rectal portion (terminating with the anal canal 314).

Figure 5:
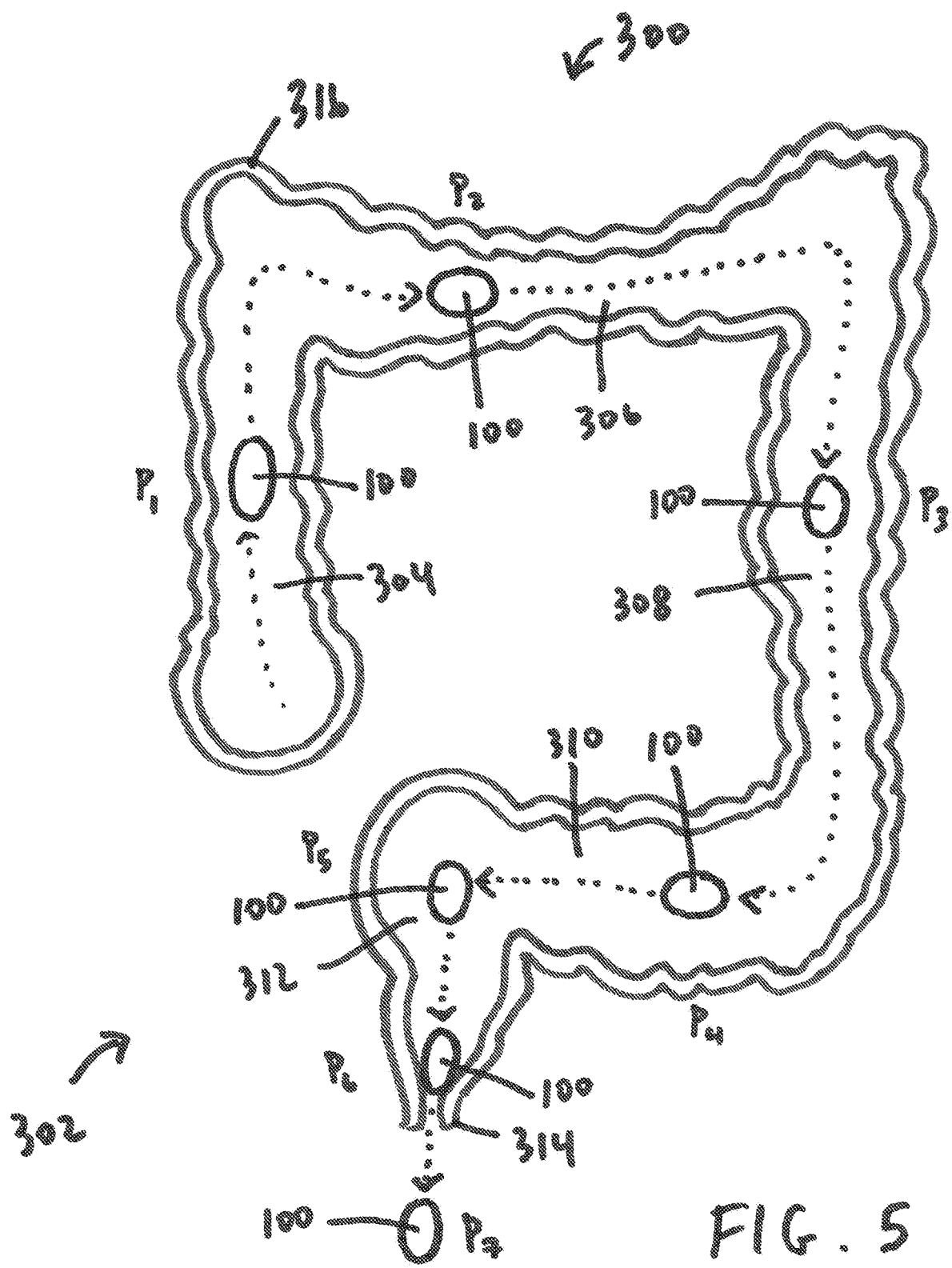
FIG. 5 shows a visual model of a large bowel showing a device moving through said large bowel and obtaining large bowel data, according to an exemplary embodiment of the present disclosure.
Figure 9:
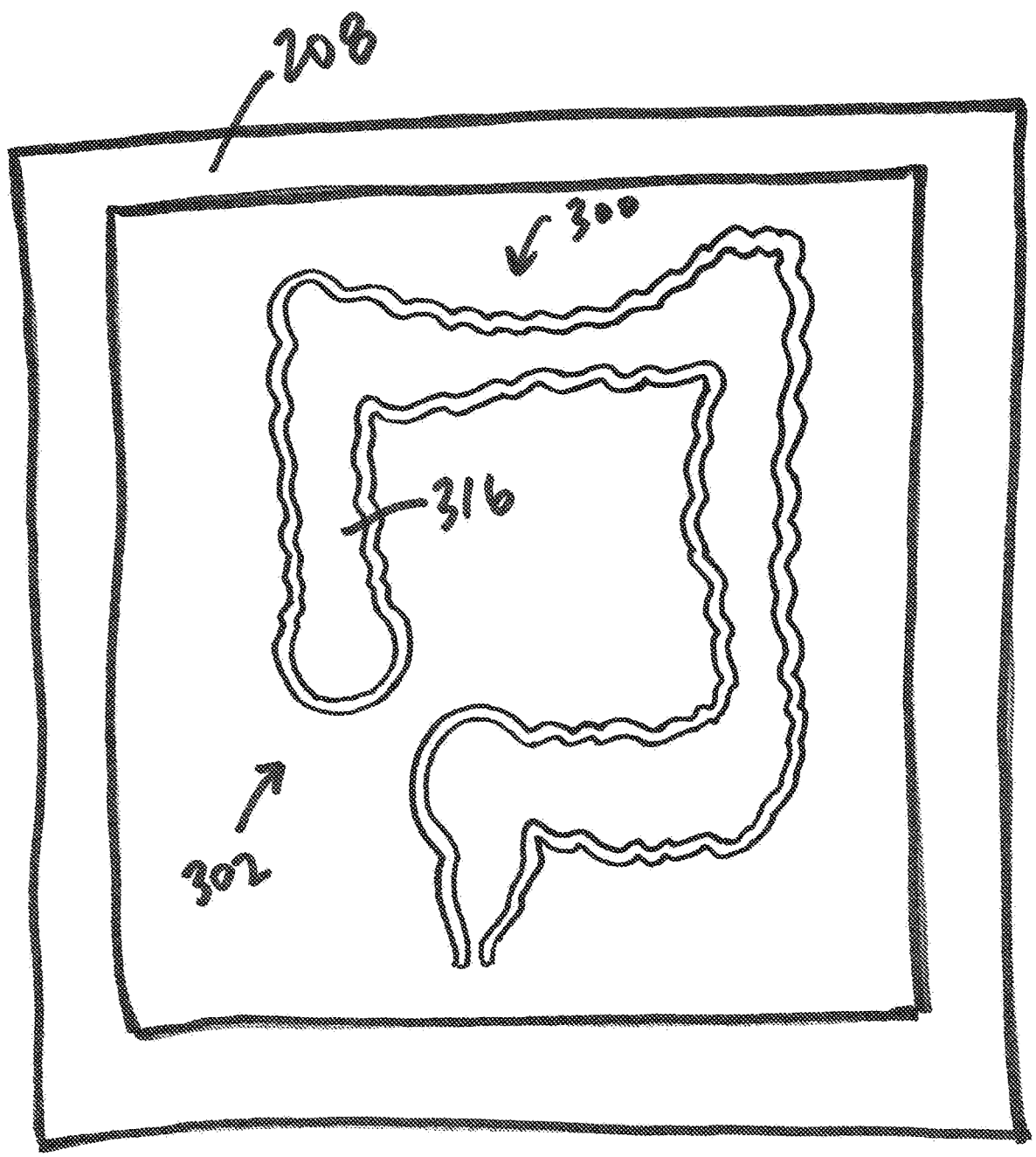
FIG. 9 shows a visual model of a large bowel depiction of a large bowel on a display, according to an exemplary embodiment of the present disclosure.

For example, and as shown in FIG. 5, an exemplary device or capsule 100 is shown as moving (indicated by the direction of the dotted arrows) from the ascending colon 304 (shown at position $P_1$), to the transverse colon 306 (shown at position $P_2$), to the descending colon 308 (shown at position $P_3$), to the sigmoid colon 310 (shown at position $P_4$), to the rectum 312 (shown at position $P_5$), to approaching the anal canal 314 (shown at position $P_6$), and ultimately expelled outside of the large bowel 316 (shown at position $P_7$). As device or capsule 100 moves through large bowel 316, it can obtain data using, for example, impedance elements 120 and/or any number of additional elements 132, each/both/all as referenced within PCT patent application serial no. PCT/US2017/044707. Said data, raw or processed, can be depicted as and/or along with a visual model 300 of a large bowel depiction 302 of a large bowel 316, or portions thereof, on a display 208, such as shown in FIG. 9.

Furthermore, computer models of stress distributions obtained from the geometry and deformation can also be computed in response to the pressure measurements obtained with the device or capsule 100, such as referenced above, and such information can also be superimposed on the patient-specific geometry depicted as or as part of visual model 300.

As additional patients undergo a procedure such as described above (generally involving the ingestion of a device or capsule 100 and monitoring the same as it moves through various parts of the digestive system, such as the large bowel 316, for example), an overall database on the generic anatomy becomes more robust/realistic and machine learning and artificial intelligence can be used to generate a greater (more realistic) the anatomy and mechanical performance of the large bowel for diagnosis and therapy.

Figure 6:
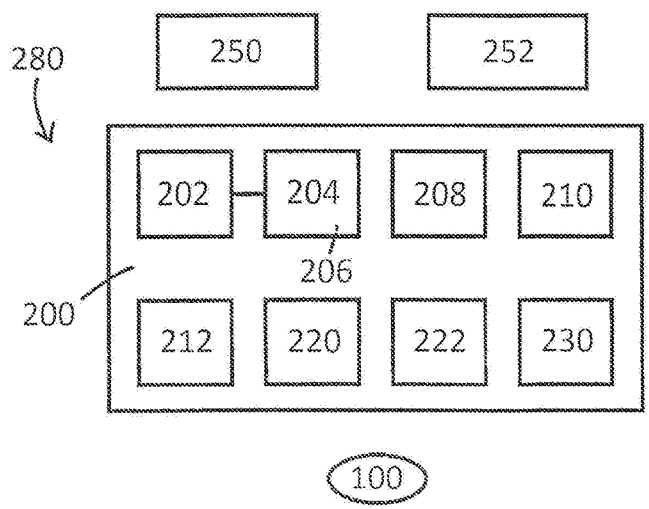
FIG. 6 shows a block component diagram of portions of a system, according to an exemplary embodiment of the present disclosure.

FIG. 6 shows a block component diagram of a console (also referred to herein as a computer) configured to obtain data from device or capsule 100, process said data, generate additional data from the processed data, and/or transmit data/instructions to device or capsule 100 to direct/facilitate operation of the same. As shown in FIG. 6, an exemplary console or computer 200 comprises a processor 202 (such as a microprocessor) connected to or otherwise in communication with a storage medium 204. Software 206 (computer instructions) can be stored within storage medium 204 and accessed by processor 202 to operate console or computer 200 as described herein. Exemplary consoles 200 of the present disclosure may further comprise a display 208 (such as a computer screen, monitor, LCD, etc.) configured to display information therein/thereon, such as to display one or more visual models 300 of large bowel depiction(s) 302 as referenced herein, and may be configured to communicate with an input device 250 (such as a mouse, keyboard, touchpad, touchscreen, stylus, microphone, smartphone, tablet, etc.), either wirelessly or via wired connection to console or computer 200, such as via input port 210. Exemplary consoles or computers 200 of the present disclosure may also be configured to communicate with an output device 252 (such as a monitor, additional screen, speaker, printer, etc.), either wirelessly or via wired connection to console or computer 200, such as via input port 212.

Figure 8:
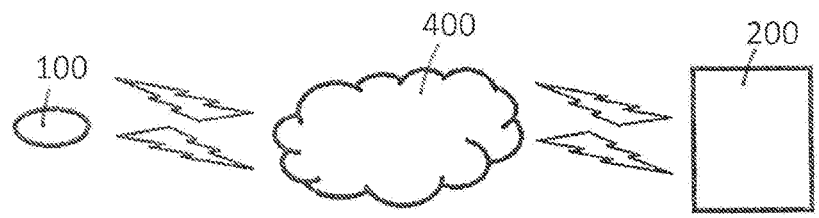
FIG. 8 shows a device and a system communicating over a network, according to an exemplary embodiment of the present disclosure.

Exemplary consoles or computers 200 of the present disclosure may further comprise a wireless transmitter 220 configured to transmit data/information to device or capsule 100, and may also comprise a wireless receiver 222 configured to receive data/information from device or capsule 100. Said data/information could include instructions for operation of various items of device or capsule 100, such as impedance element 120 (including, for example, electrodes 122, 124, 126, and/or 128), pressure sensor 130, one or more additional elements 132, wireless transmitter 140, and/or wireless receiver 142, and could also include data from said device or capsule 100, such as impedance data from impedance element 120, pressure data from pressure sensor 130, and/or pH data (such as by way of a pH sensor, an exemplary additional element 132), visual data, etc., from one or more additional elements 132, as referenced herein. Console or computer 200 can communicate directly with device or capsule 100, as referenced above, or indirectly through a network 400, such as shown in FIG. 8, such as by way of operation of a network element 230 configured to allow data/information to be transmitted between device or capsule 100 and console or computer 200 through a network 400, such as the internet or an intranet.

An exemplary system 280 of the present disclosure, as shown in FIG. 6, therefore can comprise a device or capsule 100 and a console or computer 200 and other items connected to console or computer 200, such as an input device 250 and/or an output device 252.

Figure 7:
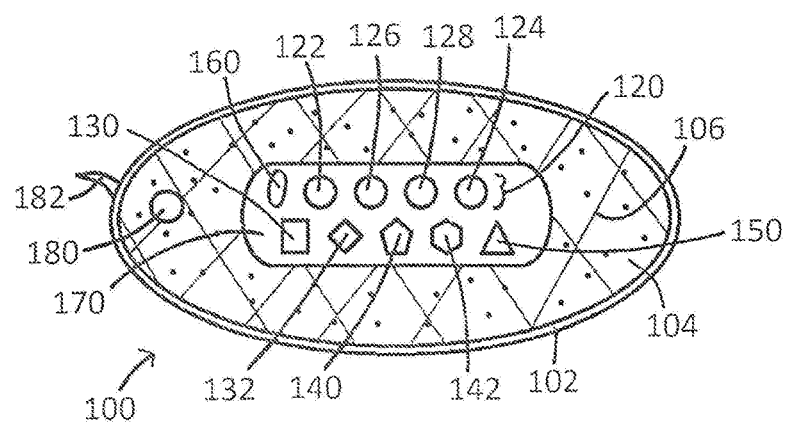
FIG. 7 shows a prior art device or capsule, according to an exemplary embodiment of the present disclosure.

FIG. 7 shows an exemplary device or capsule 100 for use with the present disclosure, as depicted in PCT patent application serial no. PCT/US2017/044707. As shown in FIG. 7, an exemplary capsule can comprise an outer shell 102 covering said device or capsule 100, whereby outer shell 102 is configured to dissolve within the stomach after being ingested or in the intestine after being inserted. An expandable material 104 is positioned within outer shell 102, so that when outer shell 102 is dissolved and liquid from within the stomach comes into contact with expandable material 104, expandable material 104 can expand after contacting said liquid. Expandable material 104 can be at least partially surrounded by a mesh 106, such as shown in FIG. 7, so that when expandable material 104 expands within the stomach, mesh 106 also expands so to retain the expandable material 104 within mesh 106. In some embodiments, expandable material 104 may comprise various pieces of expandable material 104 that are not connected to one another, and in such an embodiment, for example, mesh 106 can retain each piece of expandable material 104 within said mesh 106.

Outer shell 102 can dissolve relatively quickly after being swallowed, such as in a matter of seconds to a few minutes, ranging from 1 second to 5 minutes or longer. Expandable material 104 can expand up to, for example, two, three, four, five, ten, twenty, fifty, one hundred, or less or more, times its original size/volume, after being exposed within the stomach (after outer shell 102 has partially or fully dissolved or been partially or fully digested, for example). Expandable material 104 could expand, for example, and have an expansion length (such as from one relative side of expandable material 104 to an opposite relative side of expandable material 104) of 3 cm, 4 cm, 5 cm, 7 cm, 10 cm, or more or less. In at least one embodiment, expandable material 104 comprises a fungus, such as black fungus, that would be dry or relatively dry within device or capsule 100 at the time device or capsule 100 is swallowed. Expandable material 104, after expansion, would occupy space within the stomach that is more space than device or capsule 100 occupies right after being swallowed, and the larger space would help make the patient feel like more food is in his or her stomach, providing a feeling of satiety even though less food is ingested, for example. The patient may swallow several devices or capsules 100 at different time points to avoid that the stomach always will have the same amount of expandable material 104 inside. Mesh 106 would then be configured to retain the expanded expandable material, and various other elements of device or capsule 100, such as a substrate 170 and elements thereon or connected thereto, as referenced herein.

Devices or capsules 100 useful with the present disclosure may also be referred to and/or configured as pills, pellets, and the like, and be sized and shaped so to be readily swallowed by a patient.

In an exemplary embodiment of a device or capsule 100, the expandable material 104, or other components of device or capsule 100, contains electrochemical means for active movement inside the stomach, such as robotic arms or propellers, which can aid movement of the device or even temporarily attach it to the stomach wall. For example, and as shown in FIG. 7, an exemplary device or capsule 100 can comprise one or more movement elements 180 coupled thereto and/or embedded therein, and/or can comprise one or more attachment elements 182 coupled thereto and/or embedded therein, whereby movement elements 180, such as robotic arms, propellers, or other mechanical devices configured to facilitate movement of a device, are configured to facilitate movement of the device or capsule 100 within the stomach, and wherein attachment elements 182, configured as barbs, hooks, or the like, are configured to facilitate engagement and ultimate disengagement of device or capsule 100, as may be desired, to locations within the gastrointestinal tract.

Exemplary devices or capsules 100 useful with the present disclosure are also configured so to obtain impedance data and/or pressure data within a gastrointestinal tract. To accomplish the same, exemplary devices or capsules 100 useful with the present disclosure may comprise various electrical components, sensors, and the like, as described in further detail herein. For example, and exemplary device or capsule 100 useful with the present disclosure may comprise an impedance element 120, as shown in FIG. 7, configured to obtain impedance data within the gastrointestinal tract.

Such an impedance element 120, for example, may comprise several electrodes, such as a first excitation electrode 122 and a second excitation electrode 124 configured to generate an electric field that is detectable using a first detection electrode 126 and a second detection electrode 128, for example. Detection electrodes 126, 128 could be physically positioned in between excitation electrodes 122, 124 for example, so to obtain impedance data as desired.

Exemplary devices or capsules 100 useful with the present disclosure may contain various elements in lieu of or in addition to impedance element 120 noted above, such as, for example, a pressure sensor 130 configured to obtain pressure data within the gastrointestinal tract, and optionally one or more additional elements 132 which may comprise, for example, a camera with a light source configured to obtain visual data within a gastrointestinal tract, a pH sensor configured to obtain pH data within a gastrointestinal tract, a radiopaque marker configured to be detected using a scanner configured to detect a radiopaque marker within the body, an electromagnetic marker configured to be detected using a scanner configured to detect an electromagnetic marker within the body, a mucosa-attached electromagnetic stimulator (through non-invasive external stimulation), a gyroscopic sensor (a gyroscope) configured to obtain gyroscopic data, including but not limited to gyroscope-based angle data with the digestive tract, and/or a strain gauge and chemosensors embedded in the biological material. Said data obtained using impedance element 120, pressure sensor 130, and/or one or more additional elements 132 can be transmitted from device or capsule 100 from within the body, for example, to a console or computer 200 outside of the body, by way of a wireless transmitter 140 within said device or capsule 100. Device or capsule 100 may also receive instructions from console or computer 200, such as instructions to operate or cease operation of one or more of impedance element 120, pressure sensor 130, and/or one or more additional elements 132, using a wireless receiver 142 within said device or capsule 100. In various embodiments, wireless transmitter 140 could also receive instructions/data, so said transmitter 140 could be considered as a transmitter/receiver. As such, and in various embodiments, device or capsule 100 can transmit data/information obtained by elements of device or capsule 100, using a wireless transmitter 140, outside of the body, such as to be received by a console or computer 200, and device or capsule 100 can receive data/information from outside the body, such as from console or computer 200, by way of a wireless receiver 142. In at least some embodiments, wireless transmitter 140 may be configured to receive data/information, and/or wireless receiver 142 may be configured to transmit data/information.

In at least one embodiment, one or more additional elements 132 may comprise a printed circuit, such as a printed circuit board (PCB), which may be/comprise a substrate 170 as referenced in further detail herein, configured to measure electrical/electromyography (EMG) activity (exemplary data) within the large bowel, for example. Said data can, in various embodiments, be obtained in addition to various mechanical measurements, such as pressure data obtained by pressure sensor 130 as referenced herein, cross-sectional area (CSA) data determined by impedance data obtained using impedance element(s) 120, and potential gyroscope-based angles obtained using one or more additional elements 132. Various impedance elements 120, electrodes 122, 124, 126, 128, sensors 130, and/or additional elements 132 may be present upon or incorporated into/with one or more PCBs (exemplary additional elements 132).

In at least one embodiment of a device or capsule 100 useful with the present disclosure, said device or capsule 100 is configured to deliver electrical current to stimulate motility of the large bowel, such as to, for example, induce defecation for individuals with constipation, or to inhibit contractions for individuals with fecal incontinence, and the like. In such an embodiment, impedance elements 120 (such as electrodes 122, 124), or one or more additional elements 132 configured as an electrical stimulating element, can deliver an electric current, powered by power source 160, to stimulate motililty of the large bowel.

A computer element 150, as referenced in further detail herein, could also be positioned within device or capsule 100, and connected (via wires, traces, and/or wirelessly) to one or more of impedance element 120 (including, for example, electrodes 122, 124, 126, and/or 128), pressure sensor 130, one or more additional elements 132, wireless transmitter 140, and/or wireless receiver 142, so to, for example, control operation of said items. Computer element 150 could direct operation of said items without input from console or computer 200, and/or could direct operation of said items with input from console or computer 200, such as instructions from console or computer 200 received by wireless receiver 142 and transmitted to computer element 150.

Impedance element 120 (including, for example, electrodes 122, 124, 126, and/or 128), pressure sensor 130, one or more additional elements 132, wireless transmitter 140, wireless receiver 142, and/or computer element 150 could be powered using a power source 160, such as a battery. Power source 160 could be a single-use battery or a rechargeable battery, as may be desired. Alternative the energy supply can come from body-powered sources and elements.

Impedance element 120 (including, for example, electrodes 122, 124, 126, and/or 128), pressure sensor 130, one or more additional elements 132, wireless transmitter 140, wireless receiver 142, computer element 150, and/or power source 160 could be connected to a substrate 170, such as shown in FIG. 7. Such a substrate 170 could comprise plastic and/or metal, for example.

Devices or capsules 100 useful with the present disclosure are configured to obtain data/information with the gastrointestinal tract, including the stomach, the small intestine, the large intestine, various junctions and/or sphincters therein, and the anus, including, but not limited to, impedance data, pressure data, pH data, and other data as referenced herein. Devices or capsules 100 can be safely swallowed and excreted.

As noted above, other devices or capsules 100 can be used in connection with the present disclosure, such as the various pellets described within U.S. patent application Ser. No. 15/664,938, filed Jul. 31, 2017 and published as U.S. patent application publication no. US 2017/0340264 on Nov. 30, 2017.

Impedance data can be used to determine various measurements, such as cross-sectional areas, diameters, etc., within luminal organs, as referenced within U.S. Pat. No. 7,454,244 to Kassab et al., the contents of which are incorporated herein in their entirety by reference.

Figure 10:
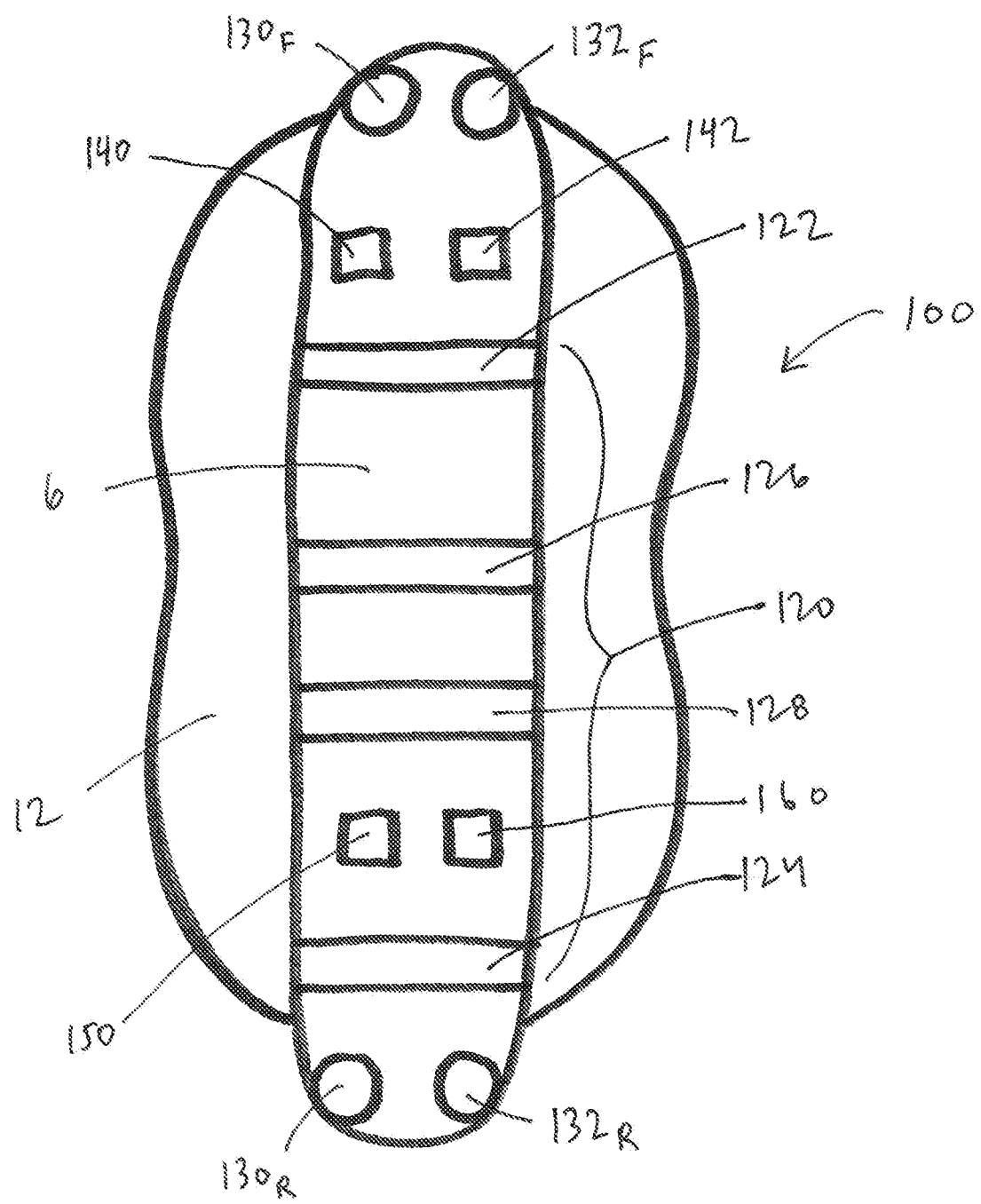
FIG. 10 shows a device having various features/components, according to an exemplary embodiment of the present disclosure.

FIG. 10 shows an exemplary device or capsule 100 used as referenced herein. As shown in FIG. 10, device or capsule 100 may comprise a central stabilizing flexible or non-flexible core rod 6 surrounded at least partially by a balloon or bag 12 configured for inflation. Various elements can present upon or within rod 6 and/or balloon or bag 12, such as, for example, a front-positioned pressure sensor 130

(identified as $130_F$ in FIG. 10), a front-positioned gyroscopic sensor 132 (an exemplary additional element 132, identified as $132_F$ in FIG. 10), a rear-positioned pressure sensor 130 (identified as $130_R$ in FIG. 10), a rear-positioned gyroscopic sensor 132 (an exemplary additional element 132, identified as $132_R$ in FIG. 10), and impedance element 120 (including, for example, electrodes 122, 124, 126, and/or 128), a wireless transmitter 140, a wireless receiver 142, a computer element 150, and/or a power source 160, for example. Such a device or capsule 100, for example, would therefore be able to obtain data/information in connection with pressure at the relative front of the device or capsule 100 (using pressure sensor $130_F$), positioning data/information at the relative front of the device or capsule 100 (using sensor $132_F$), data/information in connection with pressure at the relative rear of the device or capsule 100 (using pressure sensor $130_R$), positioning data/information at the relative rear of the device or capsule 100 (using sensor $132_R$), and/or impedance/conductance data/information within the balloon or bag 12 (using impedance element 120), to process the same as desired using computer element 150, transmit said raw and/or unprocessed data/information using wireless transmitter 140, receive data/information using wireless receiver 142, and power various components of said device or capsule 100 using power source 160.

Figure 11:
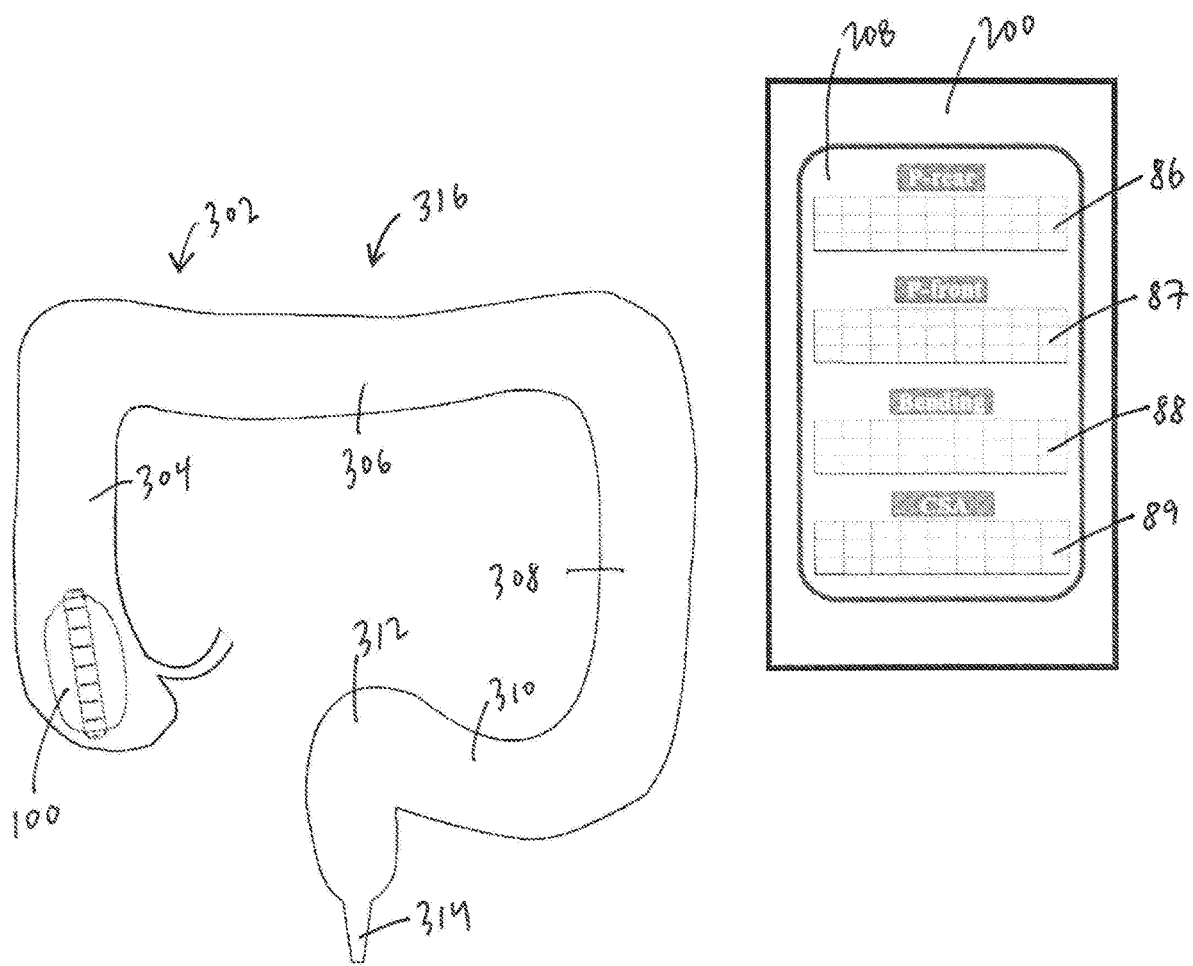
FIG. 11 shows a device positioned within the ascending colon, according to an exemplary embodiment of the present disclosure.

Use of an exemplary device or capsule 100 of the present disclosure is shown in FIGS. 11-14. As shown in FIG. 11, a device or capsule 100 is shown positioned within ascending colon 304 of a large bowel 316, with balloon or bag 12 inflated. Said device or capsule 100 can be positioned within large bowel 316 by, for example, swallowing device or capsule 100, positioning device or capsule 100 within large bowel 316 laparoscopically or surgically, such as via a cannula/trocar, delivery through the anus/rectum, etc. FIG. 11 also shows an exemplary display 208 of a console or computer 200, with various data portions shown thereon, such as a rear pressure data portion 86 ("P-rear"), a front pressure data portion 87 ("P-front"), a bending data portion 88 ("Bending"), and a cross-sectional area data portion 89 ("CSA"), whereby, for example, rear pressure data portion 86 depicts data obtained from a rear-positioned pressure sensor, front pressure data portion 87 depicts data obtained from a front-positioned pressure sensor, and bending data portion 88 and cross-sectional area data portion 89 depicts data obtained from impedance elements 120 and/or other elements/sensors of the present disclosure. A default/model version of a large bowel 316 (by way of a colon depiction 302) is shown in FIG. 11, which can also or alternatively be depicted on display 85.

Figure 12:
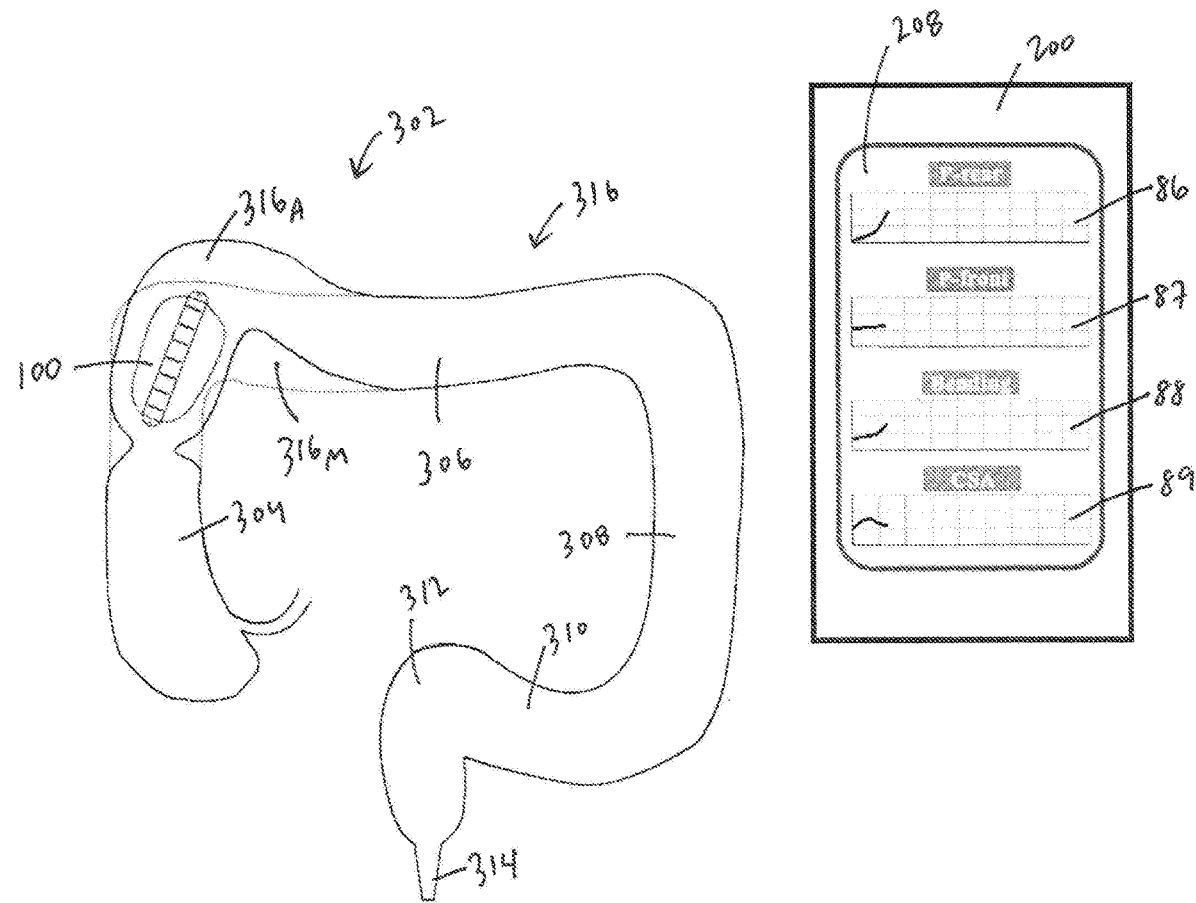
FIG. 12 shows a device moving from the ascending colon to the transverse colon and data/information obtained and transmitted in connection with the same, according to an exemplary embodiment of the present disclosure.

FIG. 12 shows device or capsule 100 moving from the position shown in FIG. 11, with data obtained during said movement. At the position shown in FIG. 12, device or capsule 100 is moving from the ascending colon 304 to the transverse colon 306, and with data on display 208 being shown in connection with data obtained by device or capsule 100. As shown on display 208, for example, rear pressure data portion 86 ("P-rear") shows increasing pressure, as, for example, portions of the large bowel constricting (such as at constriction location 275 shown in FIG. 12) to move device or capsule 100 through the large bowel 316, therefore exerting pressure on the rear-positioned pressure sensor 130. Front pressure data portion 87 ("P-front") shows relatively flat or slightly increasing pressure, as the front-positioned pressure sensor 130 has no to low pressure exerted thereon. Bending data portion 88 ("Bending") shows increased values as device or capsule 100 moves from the ascending colon 304 to the transverse colon 306, and cross-sectional area data portion 89 ("CSA") shows changes in cross-sectional area of device or capsule 100, such as within balloon or bag 12, as the device or capsule 100 moves through the large bowel 316. Colon depiction 302 may also change or otherwise be modified, such as shown in FIG. 12, such as to depict the model large bowel 316 (shown as $316_M$) and to also depict the actual person's large bowel 316 (shown as $316_A$) based on data obtained from device or capsule 100 as device or capsule 100 moves through the large bowel 316.

Figure 13:
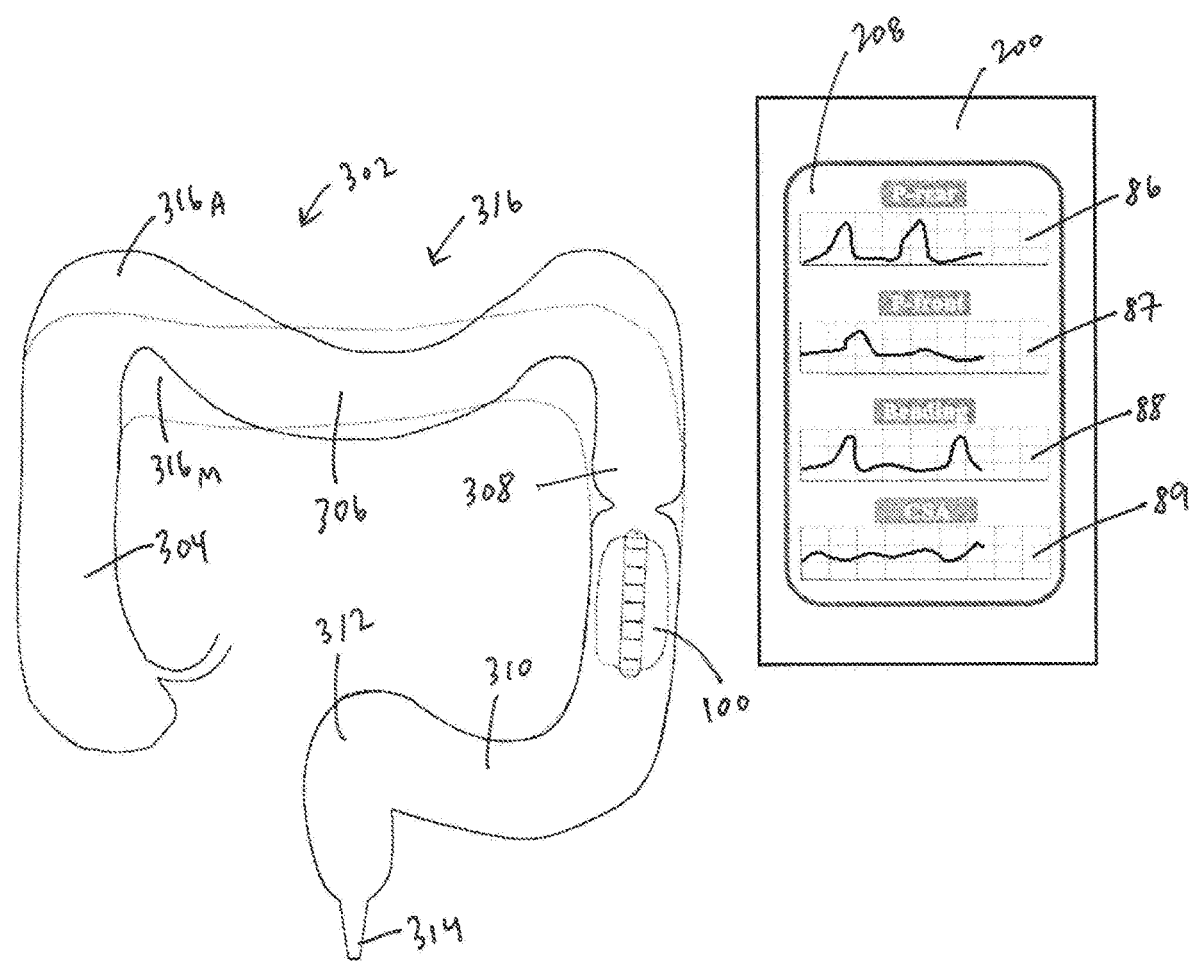
FIG. 13 shows a device in the descending colon and data/information obtained and transmitted in connection with the same, according to an exemplary embodiment of the present disclosure.

FIG. 13 shows device or capsule 100 moving from the position shown in FIG. 12, with data obtained during said movement. At the position shown in FIG. 13, device or capsule 100 has moved from the transverse colon 306 to the descending colon 308, and with data on display 208 being shown in connection with data obtained by device or capsule 100. As shown on display 208, for example, rear pressure data portion 86 ("P-rear") shows two pressure peaks, indicating high rear pressure (on the rear-positioned pressure sensor 130) as device or capsule 100 moved from the ascending colon 304 to the transverse colon 306 and from the transverse colon 306 to the descending colon 308. Front pressure data portion 87 ("P-front"), bending data portion 88 ("Bending"), and cross-sectional area data portion 89 ("CSA") show changes in front pressure, bending, and CSA, respectively, as device or capsule 100 moved through the large bowel 316 (with data obtained at various locations over time, with time being generally on the x-axis of each of 86, 87, 88, and 89). Colon depiction 302 may also change or otherwise be modified, such as shown in FIG. 13, such as to depict the model large bowel 316 (shown as $316_M$) and to also depict the actual person's large bowel 316 (shown as $316_A$) based on data obtained from device or capsule 100 as device or capsule 100 moves through the large bowel 316.

Figure 14:
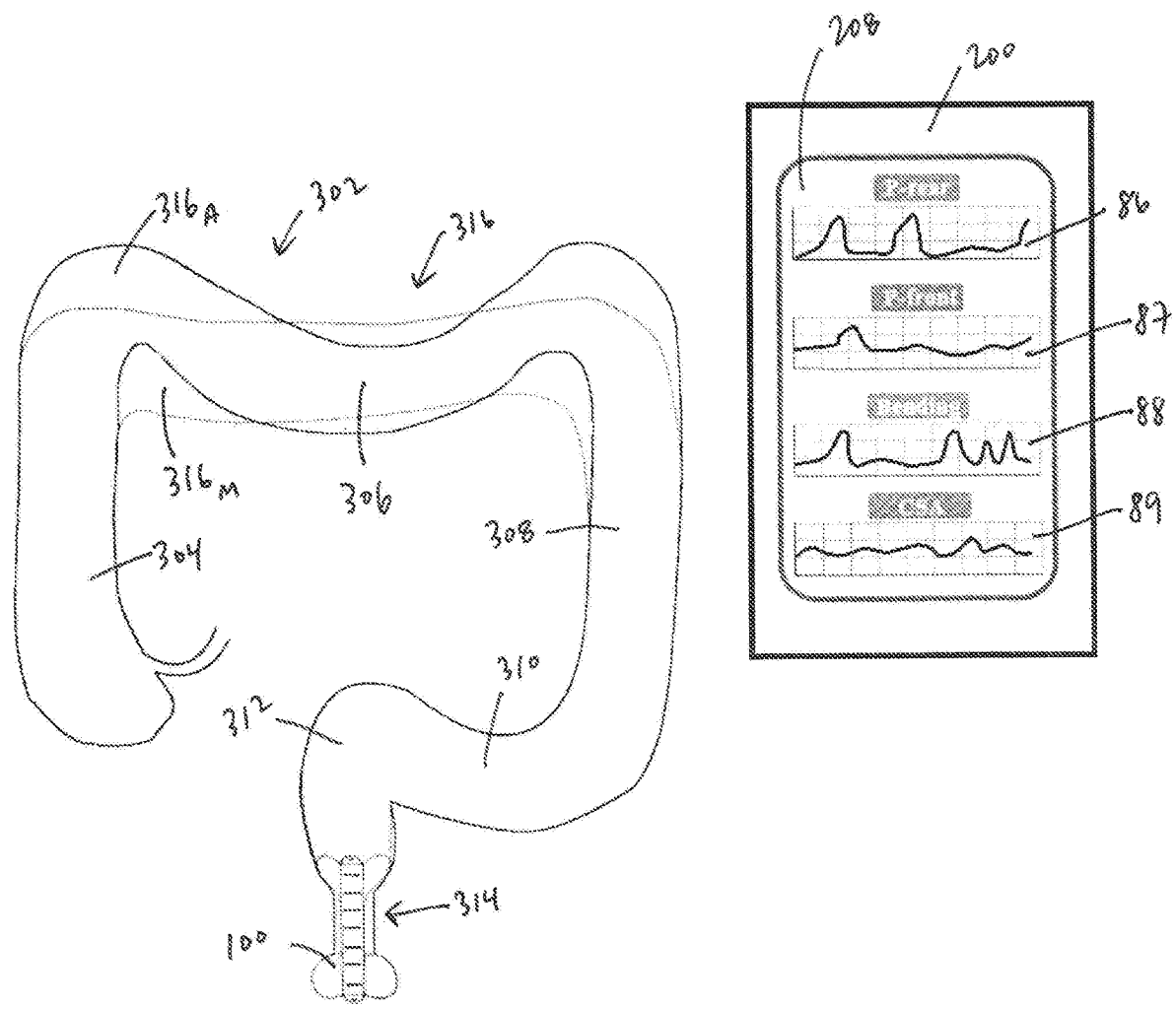
FIG. 14 shows a device in the anal canal and data/information obtained and transmitted in connection with the same, according to an exemplary embodiment of the present disclosure.

FIG. 14 shows device or capsule 100 moving from the position shown in FIG. 13, with data obtained during said movement. At the position shown in FIG. 14, device or capsule 100 has moved from the descending colon 308 to the sigmoid colon 310, to the rectum 312, and is being expelled through the anal canal 314, with data on display 208 being shown in connection with data obtained by device or capsule 100. As shown on display 208, for example, rear pressure data portion 86 ("P-rear"), front pressure data portion 87 ("P-front"), bending data portion 88 ("Bending"), and cross-sectional area data portion 89 ("CSA") each show changes in rear pressure, front pressure, bending, and CSA, respectively, as device or capsule 100 moved through the large bowel 316 (with data obtained at various locations over time, with time being generally on the x-axis of each of 86, 87, 88, and 89). Colon depiction 302 may also change or otherwise be modified, such as shown in FIG. 14, such as to depict the model large bowel 316 (shown as $316_M$) and to also depict the actual person's large bowel 316 (shown as $316_A$) based on data obtained from device or capsule 100 as device or capsule 100 moves through the large bowel 316.

Figure 15:
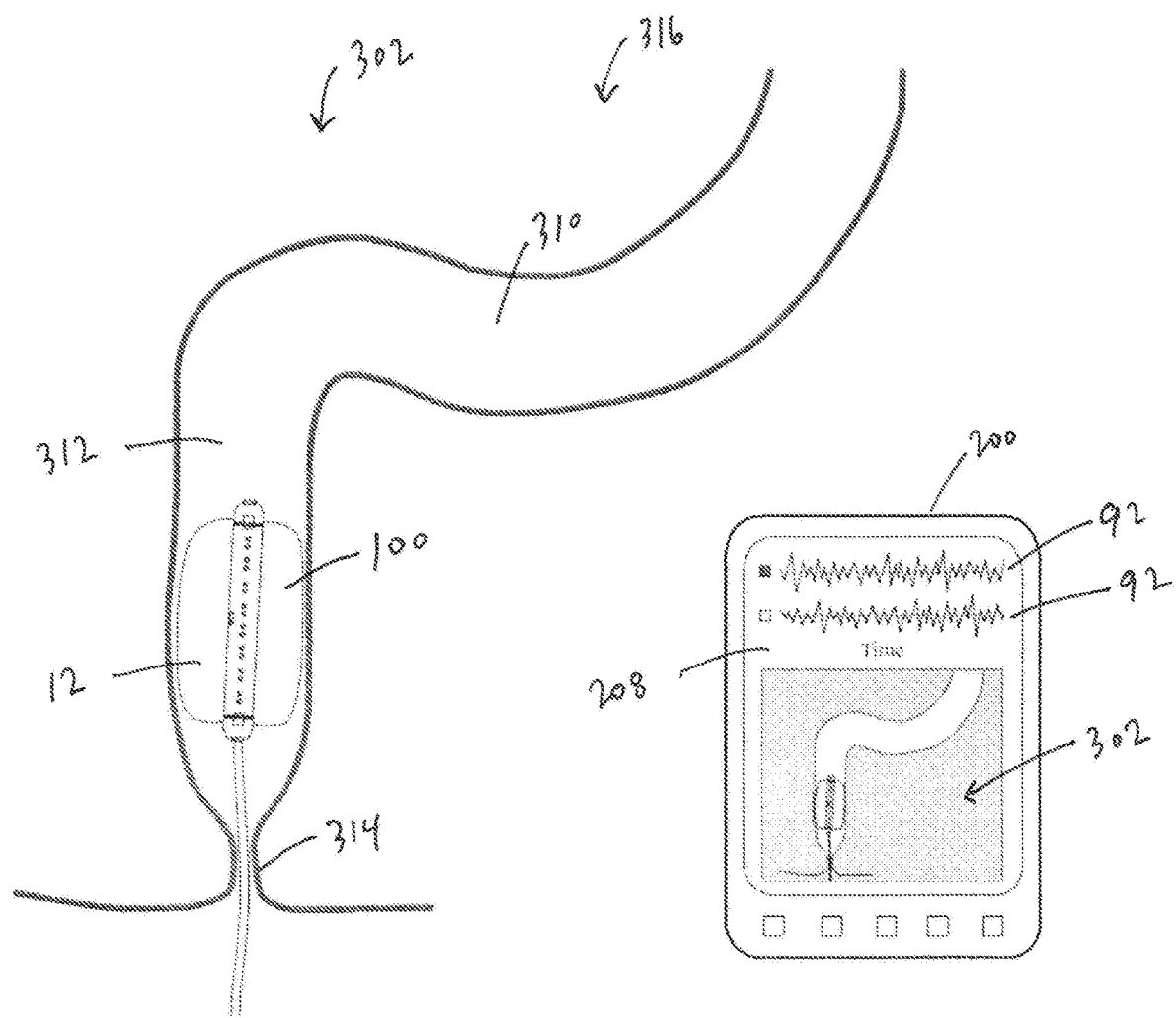
FIG. 15 shows a device in the rectum and data/information obtained and transmitted in connection with the same, according to an exemplary embodiment of the present disclosure.

FIG. 15 shows the use of an exemplary device or capsule 100 to obtain data in connection with the defecation process. As shown in FIG. 15, device or capsule 100 is show in the rectum 312, positioned therein through the anal canal 314. A tube 17 is shown attached to device or capsule 100, so that the balloon or bag 12 of device or capsule 100 can be filled with a liquid or a gas 28 via tube 17. Device or capsule 100 is shown as being filled with a liquid or a gas 28. FIG. 15 also shows an exemplary display 208 of a console or computer 200, showing various data or information thereon (with the data shown in this figure as an exemplary jagged line and not specifically tied to any particular obtained data), including, for example, a colon depiction 302 and/or rear pressure data portion 86, front pressure data portion 87, bending data portion 88, and/or cross-sectional area data portion 89 as referenced herein. Data portions 92 are shown in FIG. 15, are intended to include one or more of rear pressure data portion 86, front pressure data portion 87, bending data portion 88, and/or cross-sectional area data portion 89 as referenced herein.

Figure 16:
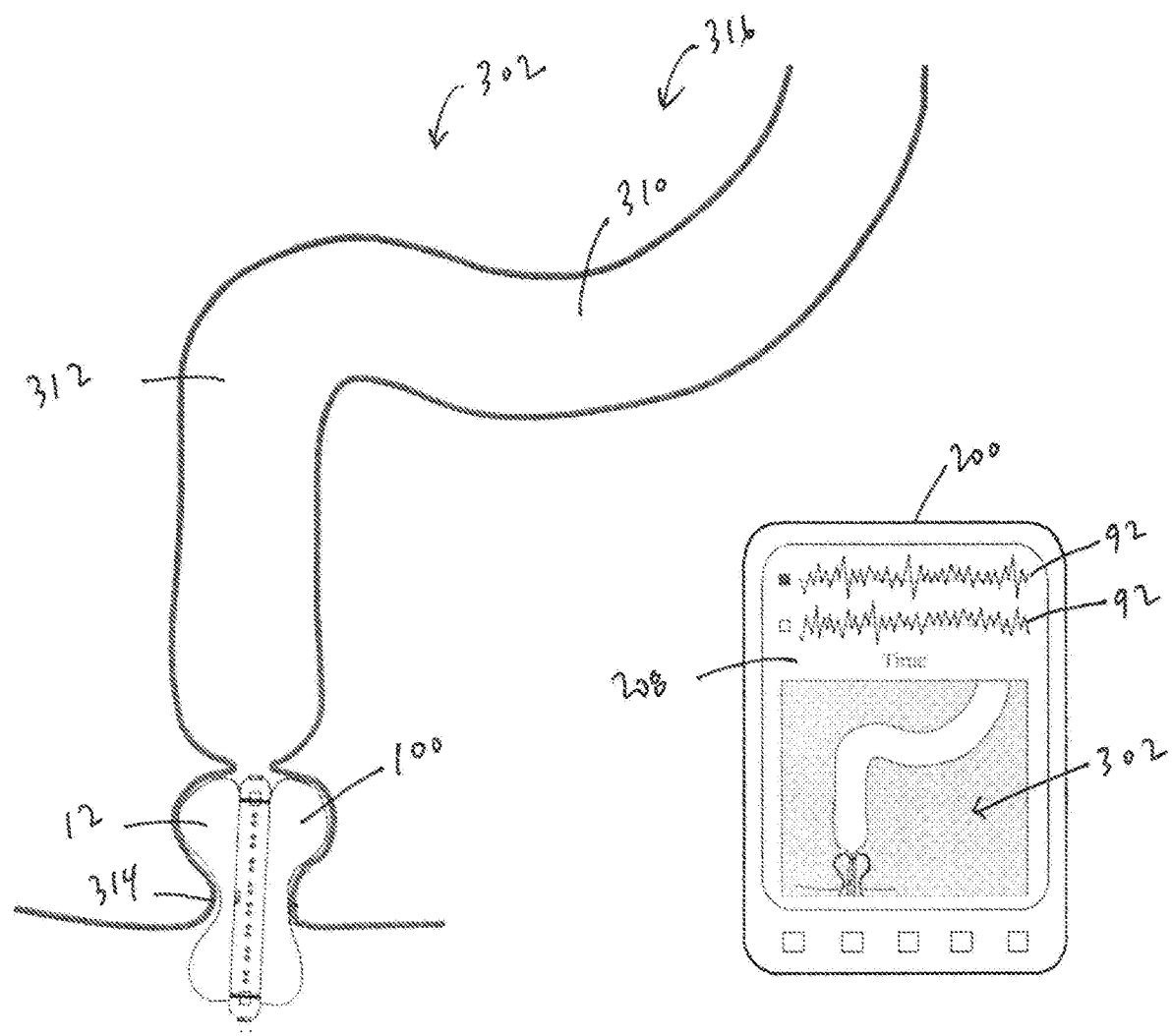
FIG. 16 shows a device in the anal canal and data/information obtained and transmitted in connection with the same, according to an exemplary embodiment of the present disclosure.

FIG. 16 shows the use of an exemplary device or capsule 100 to obtain data in connection with the defecation process. As shown in FIG. 16, device or capsule 100 is show in the anal canal 314, being expelled. FIG. 16 also shows an exemplary display 208 of a console or computer 200, showing various data or information thereon (with the data shown in this figure as an exemplary jagged line and not specifically tied to any particular obtained data), including, for example, a colon depiction 302 and/or rear pressure data portion 86, front pressure data portion 87, bending data portion 88, and/or cross-sectional area data portion 89 as referenced herein. Data portions 92 are shown in FIG. 15, are intended to include one or more of rear pressure data portion 86, front pressure data portion 87, bending data portion 88, and/or cross-sectional area data portion 89 as referenced herein, such as during defecation.

FIG. 17 shows an exemplary method of positioning a device or capsule 100 of the present disclosure within a large bowel 316. As shown therein, a device or capsule 100 is present within the ascending colon 304, but could be positioned in other portions of the large bowel 316, such as within the transverse colon 306, the descending colon 308, the sigmoid colon 310, or the rectum 312. Device or capsule 100 can, for example, be inserted through the anal canal 314 using an insertion device 95 configured to engage device or capsule 100 and further configured to be navigated within the large bowel 316 to a location of interest therein. A tube 17 can also be connected to device or capsule 100, so that when device or capsule 100 is positioned at a location of interest, the balloon or bag 12 of device or capsule 100 can be filled with a liquid or a gas 28 via tube 17, such as shown in FIG. 18. After device or capsule 100 is positioned, for example, insertion device 95 can be released therefrom and removed (such as depicted in FIG. 18), and after balloon or bag 12 of device or capsule 100 is filled with a liquid or gas 28 (as depicted in FIG. 18), tube 17 can also be removed, and device or capsule 100 can be operated to obtain data as referenced herein as it moves through the large bowel 316.

Means/mechanisms other than gyroscopes and/or accelerometers (referred to herein as gyroscopic sensors 132) for determination of device or capsule 100 position with the large bowel are also disclosed herein, such as, for example, magnetic tracking (such as by way of use of one or more magnets or magnetically-attractive elements 33 of device or capsule 100, such as shown in FIG. 10) and/or the use of ultrasound, sound or radiofrequency (RF) signals (obtained from one or more sound or other wavelength transducers 355, also such as shown in FIG. 10) where the various transducers or sensors can be built into the device or capsule 100 and tracked from outside the body, such as by way of a console or computer 200 (or other device) configured to receive data/information from said transducers or sensors.

While various embodiments of devices, systems, and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method of generating a gastrointestinal model, comprising the steps of:
    delivering a device to a mammalian gastrointestinal tract, the device configured to fit within the mammalian gastrointestinal tract and comprising an outer shell configured to dissolve or otherwise be digested within the gastrointestinal tract, and further comprising a central stabilizing core at least partially surrounded by a balloon or bag, a front-positioned pressure sensor, a front-positioned gyroscopic sensor, a rear-positioned pressure sensor, a rear-positioned gyroscopic sensor, and a wireless transmitter;
    operating the device to obtain size data of the mammalian gastrointestinal tract as the device travels through at least a portion of the gastrointestinal tract during functioning of the gastrointestinal tract, wherein the step of obtaining size data comprises the steps of obtaining ascending colon size data, obtaining transverse colon size data, obtaining descending colon size data, obtaining sigmoid colon size data, obtaining rectum size data, and obtaining anal canal size data during defecation of the device;
    modifying a model colon using the obtained size data to generate a patient-specific colon model, wherein the step of modifying the model colon is performed using a console or computer having a processor connected or otherwise in communication with a storage medium, whereby computer instructions stored within the storage medium are accessible by the processor to operate the console or computer to obtain the size data from the device and to process the same to modify the model colon and to display the patient-specific colon model on an output device operably connected to or formed as part of the console or computer.

2. The method of claim 1, wherein the obtained size data comprises data obtained at a first location and at a second location within the gastrointestinal tract, and wherein the step of modifying the model colon is performed by modifying the model colon to reflect a distance between the first location and the second location so that the generated patient-specific colon model includes an indication of the distance therein.

3. The method of claim 1, wherein the size data is obtained from the device wirelessly.

4. The method of claim 1, further comprising the step of:
    obtaining additional data within the mammalian gastrointestinal tract, the additional data selected from the group consisting of impedance data obtained using an impedance element, pressure data obtained using a pressure sensor, pH data obtained using a pH sensor, and visual data obtained using a camera.

5. A device configured to perform the method of claim 1, the device comprising:
   an impedance element configured to obtain impedance data within the mammalian gastrointestinal tract.

6. The device of claim 5, further comprising:
   a power source configured to power at least one of the front-positioned pressure sensor, the front-positioned gyroscopic sensor, the rear-positioned pressure sensor, the rear-positioned gyroscopic sensor, the impedance element, and/or the wireless transmitter.

7. A method of generating a gastrointestinal model, comprising the steps of:
   delivering a device to a mammalian gastrointestinal tract, the device configured to fit within the mammalian gastrointestinal tract and comprising an outer shell configured to dissolve or otherwise be digested within the gastrointestinal tract, and further comprising a central stabilizing core at least partially surrounded by a balloon or bag, a front-positioned pressure sensor, a front-positioned gyroscopic sensor, a rear-positioned pressure sensor, a rear-positioned gyroscopic sensor, and a wireless transmitter;
   operating the device to obtain size data of the mammalian gastrointestinal tract as the device travels through at least a portion of the gastrointestinal tract during functioning of the gastrointestinal tract;
   modifying a model colon using the obtained size data to generate a patient-specific colon model, wherein the step of modifying the model colon is performed using a console or computer having a processor connected or otherwise in communication with a storage medium, whereby computer instructions stored within the storage medium are accessible by the processor to operate the console or computer to obtain the size data from the device and to process the same to modify the model colon and to display the patient-specific colon model on an output device operably connected to or formed as part of the console or computer,
   wherein the obtained size data comprises at least one diameter obtained within the gastrointestinal tract, and wherein the step of modifying the model colon is performed by modifying the model colon at a corresponding location of the device when the at the least one diameter is obtained so that the generated patient-specific colon model includes an indication of the at least one diameter therein.

8. A method of generating a gastrointestinal model, comprising the steps of:
   delivering a device to a mammalian gastrointestinal tract, the device configured to fit within the mammalian gastrointestinal tract and comprising an outer shell configured to dissolve or otherwise be digested within the gastrointestinal tract, and further comprising a central stabilizing core at least partially surrounded by a balloon or bag, a front-positioned pressure sensor, a front-positioned gyroscopic sensor, a rear-positioned pressure sensor, a rear-positioned gyroscopic sensor, and a wireless transmitter;
   operating the device to obtain size data of the mammalian gastrointestinal tract as the device travels through at least a portion of the gastrointestinal tract during functioning of the gastrointestinal tract;
   modifying a model colon using the obtained size data to generate a patient-specific colon model, wherein the step of modifying the model colon is performed using a console or computer having a processor connected or otherwise in communication with a storage medium, whereby computer instructions stored within the storage medium are accessible by the processor to operate the console or computer to obtain the size data from the device and to process the same to modify the model colon and to display the patient-specific colon model on an output device operably connected to or formed as part of the console or computer,
   wherein the obtained size data comprises at least one cross-sectional area obtained within the gastrointestinal tract, and wherein the step of modifying the model colon is performed by modifying the model colon at a corresponding location of the device when the at the least one cross-sectional area is obtained so that the generated patient-specific colon model includes an indication of the at least one cross-sectional area therein.

* * * * *